(12) United States Patent
Fruchey et al.

(10) Patent No.: US 8,466,300 B2
(45) Date of Patent: *Jun. 18, 2013

(54) PROCESSES FOR THE PRODUCTION OF HYDROGENATED PRODUCTS

(75) Inventors: Olan S. Fruchey, Hurricane, WV (US);
Leo E. Manzer, Wilmington, DE (US);
Dilum Dunuwila, Princton, NJ (US);
Brian Terry Keen, Pinch, WV (US);
Brooke Ashley Albin, Charleston, WV (US);
Nye A. Clinton, Hurricane, WV (US);
Bernard Duane Dombek, Charleston, WV (US)

(73) Assignee: BioAmber International S.a.r.l., Luxembourg (LU)

( * ) Notice: Subject to any disclaimer, the term of this patent is extended or adjusted under 35 U.S.C. 154(b) by 52 days.

This patent is subject to a terminal disclaimer.

(21) Appl. No.: 13/051,579

(22) Filed: Mar. 18, 2011

(65) Prior Publication Data

US 2011/0245514 A1 Oct. 6, 2011

Related U.S. Application Data

(60) Provisional application No. 61/320,081, filed on Apr. 1, 2010.

(51) Int. Cl.
*C07D 307/00* (2006.01)
*C07D 305/00* (2006.01)
*C07C 27/04* (2006.01)

(52) U.S. Cl.
USPC ............................ 549/326; 549/508; 568/864

(58) Field of Classification Search
USPC .................................... 549/326, 508; 568/864
See application file for complete search history.

(56) References Cited

U.S. PATENT DOCUMENTS

| 4,782,167 A | 11/1988 | Rao |
| 5,034,105 A | 7/1991 | Berglund et al. |
| 5,143,833 A | 9/1992 | Datta |
| 5,958,744 A | 9/1999 | Berglund et al. |
| 6,245,538 B1 | 6/2001 | Wenzel et al. |
| 6,265,190 B1 | 7/2001 | Yedur et al. |
| 6,288,275 B1 | 9/2001 | Turner |
| 6,660,505 B2 | 12/2003 | Staley |
| 7,186,856 B2 | 3/2007 | Meng et al. |
| 7,217,837 B2 | 5/2007 | Isotani |
| 8,084,626 B1 * | 12/2011 | Fruchey et al. ............... 549/326 |
| 2005/0070738 A1 | 3/2005 | Isotani |
| 2006/0276674 A1 | 12/2006 | Kushiku et al. |
| 2007/0161816 A1 | 7/2007 | Isotani |
| 2010/0094051 A1 | 4/2010 | Nishi et al. |

FOREIGN PATENT DOCUMENTS

| DE | 27 18 363 A1 | 10/1978 |
| JP | 2005-132836 A | 5/2005 |
| JP | 2005-139156 | 6/2005 |
| JP | 2007-254354 A | 10/2007 |
| JP | 2008-056624 A | 3/2008 |
| JP | 2010-142191 A | 7/2010 |
| WO | 2009/082050 A1 | 7/2009 |

OTHER PUBLICATIONS

Datsenko, K.A. et al., "One-Step Inactivation of Chromosomal Genes in *Escherichia coli* K-12 Using PCR Products," *Proc. Natl. Acad. Sci.*, Jun. 6, 2000, vol. 97, No. 12, pp. 6640-6645.

Bochner, B.R. et al., "Positive Selection for Loss of Tetracycline Resistance," *Journal of Bacteriology*, Aug. 1980, vol. 143, No. 2, pp. 926-933.

Sundaramurthi, P. et al., "Calorimetric and Diffractometric Evidence for the Sequential Crystallization of Buffer Components and the Consequential pH Swing in Frozen Solutions,"*J. Phys Chem B*, 2010, vol. 114, pp. 4915-4923.

Sundaramurthi, P. et al., "'pH Swing' in Frozen Solutions—Consequence of Sequential Crystallization of Buffer Components," *The Journal of Physical Chemistry Letters*, 2010, vol. 1, pp. 265-268.

Vanderzee, C.F. et al., "Enthalpies of Formation of Mono- and Diammonium Succistes and of Aqueous Ammonia and Ammonium Ion," *J. Chem. Thermodynamics*, 1972, vol. 4, pp. 541-550.

Bechthold, I. et al., "Succinic Acid: A New Platform Chemical for Biobased Polymers from Renewable Resources," *Chem. Eng. Technol.*, 2008. vol. 31, No. 5, pp. 647-654.

Kurzrock, T. et al., "Recovery of Succinic Acid from Fermentation Broth," *Biotechnol. Lett.*, 2010, vol. 32, pp. 331-339.

Mckinlay, J.B. et al., "Prospects for a Bio-Based Succinate Industry," *App. Microbiol. Biotechnol.*, 2007, vol. 76, pp. 727-740.

* cited by examiner

*Primary Examiner* — Nizal Chandrakumar
(74) *Attorney, Agent, or Firm* — DLA Piper LLP (US)

(57) ABSTRACT

A process for making a hydrogenated product includes providing a clarified DAS-containing fermentation broth; distilling the broth under super atmospheric pressure at a temperature of >100° C. to about 300° C. to form an overhead that includes water and ammonia, and a liquid bottoms that includes SA, and at least about 20 wt % water; cooling the bottoms to a temperature sufficient to cause the bottoms to separate into a liquid portion in contact with a solid portion that is substantially pure SA; separating the solid portion from the liquid portion; recovering the solid portion; hydrogenating the solid portion in the presence of at least one hydrogenation catalyst to produce the hydrogenated product including at least one of THF, GBL or BDO; and recovering the hydrogenated product.

1 Claim, 3 Drawing Sheets

PROCESSES FOR THE PRODUCTION OF HYDROGENATED PRODUCTS

RELATED APPLICATION

This application claims the benefit of U.S. Provisional Application No. 61/320,081, filed Apr. 1, 2010, the subject matter of which is hereby incorporated by reference.

TECHNICAL FIELD

This disclosure relates to processes for producing hydrogenated products, particularly 1,4-butanediol (BDO), tetrahydrofuran (THF), and gamma-butyrolactone (GBL) from succinic acid (SA) produced by fermentation.

BACKGROUND

Certain carbonaceous products of sugar fermentation are seen as replacements for petroleum-derived materials for use as feedstocks for the manufacture of carbon-containing chemicals. One such product is MAS.

A material related to MAS, namely SA, can be produced by microorganisms using fermentable carbon sources such as sugars as starting materials. However, most commercially viable, succinate producing microorganisms described in the literature neutralize the fermentation broth to maintain an appropriate pH for maximum growth, conversion and productivity. Typically, the pH of the fermentation broth is maintained at or near a pH of 7 by introduction of ammonium hydroxide into the broth, thereby converting the SA to DAS. The DAS must be converted to MAS to derive MAS from the fermentation broth.

Kushiki (Japanese Published Patent Application, Publication No. 2005-139156) discloses a method of obtaining MAS from an aqueous solution of DAS that could be obtained from a fermentation broth to which an ammonium salt is added as a counter ion. Specifically, MAS is crystallized from an aqueous solution of DAS by adding acetic acid to the solution to adjust the pH of the solution to a value between 4.6 and 6.3, causing impure MAS to crystallize from the solution.

Masuda (Japanese Unexamined Application Publication P2007-254354, Oct. 4, 2007) describes partial deammoniation of dilute aqueous solutions of "ammonium succinate" of the formula $H_4NOOCCH_2CH_2COONH_4$. From the molecular formula disclosed, it can be seen that "ammonium succinate" is diammonium succinate. Masuda removes water and ammonia by heating solutions of the ammonium succinate to yield a solid SA-based composition containing, in addition to ammonium succinate, at least one of monoammonium succinate, succinic acid, monoamide succinate, succinimide, succinamide or ester succinate. Thus, it can be inferred that like Kushiki, Masuda discloses a process that results in production of impure MAS. The processes of both Kushiki and Masuda lead to materials that need to be subjected to various purification regimes to produce high purity MAS.

Bio-derived SA such as that derived from MAS is a platform molecule for synthesis of a number of commercially important chemicals and polymers. Therefore, it is highly desirable to provide a purification technology that offers flexibility to integrate clear, commercially viable paths to derivatives such as BDO, THF and GBL. In response to the lack of an economically and technically viable process solution for converting fermentation-derived SA to BDO, THF, and GBL, it could be helpful to provide methods for providing a cost effective SA stream of sufficient purity for direct hydrogenation.

SUMMARY

We provide a process for making a hydrogenated product including providing a clarified DAS-containing fermentation broth, distilling the broth under super atmospheric pressure at a temperature of greater than 100° C. to about 300° C. to form an overhead that comprises water and ammonia, and a liquid bottoms that comprises SA, and at least about 20 wt % water, cooling and/or evaporating the bottoms to attain a temperature and composition sufficient to cause the bottoms to separate into a liquid portion and a solid portion that is substantially pure SA, separating the solid portion from the liquid portion, recovering the solid portion, hydrogenating the solid portion in the presence of at least one hydrogenation catalyst to produce the hydrogenated product comprising at least one of THF, GBL and BDO, and recovering the hydrogenated product.

We also provide a process for making a hydrogenated product including providing a clarified DAS-containing fermentation broth, adding an ammonia separating solvent and/or a water azeotroping solvent to the broth, distilling the broth at a temperature and pressure sufficient to form an overhead that comprises water and ammonia, and a liquid bottoms that comprises SA and at least about 20 wt % water, cooling and/or evaporating the bottoms to attain a temperature and composition sufficient to cause the bottoms to separate into a liquid portion and a solid portion that is substantially pure SA, separating the solid portion from the liquid portion, recovering the solid portion, hydrogenating the solid portion with hydrogen in the presence of at least one hydrogenation catalyst to produce the hydrogenated product comprising at least one of THF, GBL and BDO, and recovering the hydrogenated product.

We further provide a process for making a hydrogenated product including providing a clarified MAS-containing fermentation broth, distilling the broth under super atmospheric pressure at a temperature of >100° C. to about 300° C. to form an overhead that comprises water and ammonia, and a liquid bottoms that comprises SA and at least about 20 wt % water, cooling and/or evaporating the bottoms to attain a temperature and composition sufficient to cause the bottoms to separate into a liquid portion and a solid portion that is substantially pure SA, separating the solid portion from the liquid portion, recovering the solid portion, hydrogentating the solid portion in the presence of at least one hydrogenation catalyst to product the hydrogenated product comprising at least one of THF, GBL and BDO, and recovering the hydrogenated product.

We still further provide a process for making a hydrogenated product including providing a clarified MAS-containing fermentation broth including adding an ammonia separating solvent and/or a water azeotroping solvent to the broth, distilling the broth at a temperature and pressure sufficient to form an overhead that includes water and ammonia, and a liquid bottoms that comprises SA, and at least about 20 wt % water, cooling and/or evaporating the bottoms to attain a temperature and composition sufficient to cause the bottoms to separate into a liquid portion and a solid portion that is substantially pure SA, separating the solid portion from the liquid portion, recovering the solid portion, hydrogentating the solid portion in the presence of at least one hydrogenation catalyst to product the hydrogenated product comprising at least one of THF, GBL and BDO, and recovering the hydrogenated product.

DETAILED DESCRIPTION

Figure 1:
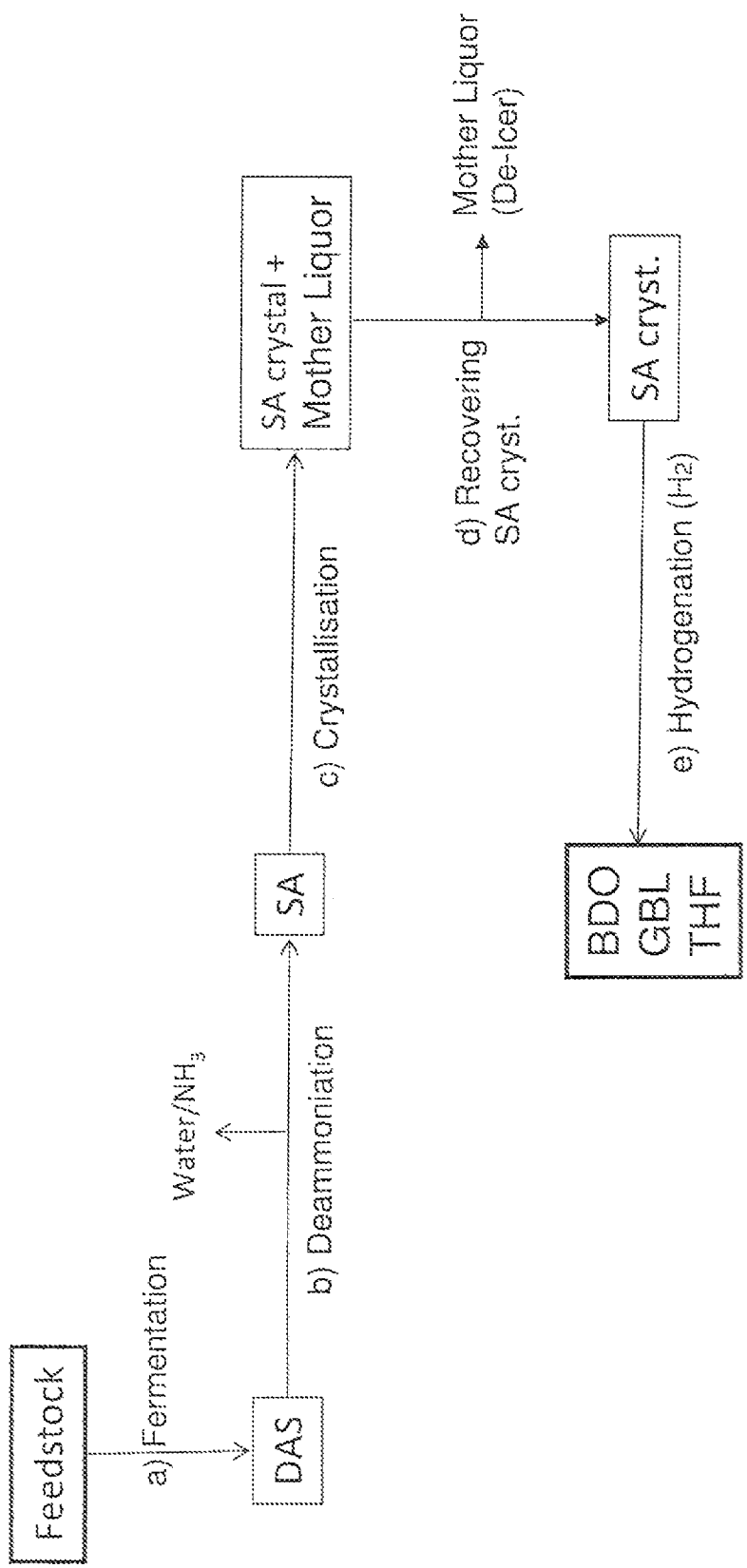
FIG. 1 schematically illustrates a fully integrated process for the hydrogenation of fermentation-derived SA to BDO, THF and GBL and depicts single-stage deammoniation of DAS to SA.

It will be appreciated that at least a portion of the following description is intended to refer to representative examples of processes selected for illustration in the drawings and is not intended to define or limit the disclosure, other than in the appended claims.

Our processes may be appreciated by reference to FIG. 1, which shows in block diagram form one representative example of our methods.

A growth vessel, typically an in-place steam sterilizable fermentor, may be used to grow a microbial culture that is subsequently utilized for the production of the DAS-containing fermentation broth. Such growth vessels are known in the art and are not further discussed.

The microbial culture may comprise microorganisms capable of producing SA from fermentable carbon sources such as carbohydrate sugars. Representative examples of microorganisms include *Escherichia coli* (*E. coli*), *Aspergillus niger, Corynebacterium glutamicum* (also called *Brevibacterium flavum*), *Enterococcus faecalis, Veillonella parvula, Actinobacillus succinogenes, Mannheimia succiniciproducens, Anaerobiospirillum succiniciproducens, Paecilomyces Varioti, Saccharomyces cerevisiae, Bacteroides fragilis, Bacteroides ruminicola, Bacteroides amylophilus, Alcaligenes eutrophus, Brevibacterium ammoniagenes, Brevibacterium lactofermentum, Candida brumptii, Candida catenulate, Candida mycoderma, Candida zeylanoides, Candida paludigena, Candida sonorensis, Candida utilis, Candida zeylanoides, Debaryomyces hansenii, Fusarium oxysporum, Humicola lanuginosa, Kloeckera apiculata, Kluyveromyces lactis, Kluyveromyces wickerhamii, Penicillium simplicissimum, Pichia anomala, Pichia besseyi, Pichia media, Pichia guilliermondii, Pichia inositovora, Pichia stipidis, Saccharomyces bayanus, Schizosaccharomyces pombe, Torulopsis candida, Yarrowia lipolytica*, mixtures thereof and the like.

A preferred microorganism is an *E. coli* strain deposited at the ATCC under accession number PTA-5132. More preferred is this strain with its three antibiotic resistance genes (cat, amphl, tetA) removed. Removal of the antibiotic resistance genes cat (coding for the resistance to chloramphenicol), and amphl (coding for the resistance to kanamycin) can be performed by the so-called "Lambda-red (λ-red)" procedure as described in Datsenko K A and Wanner B L., Proc. Natl. Acad. Sci. USA 2000 Jun. 6; 97(12) 6640-5, the subject matter of which is incorporated herein by reference. The tetracycline resistant gene tetA can be removed using the procedure originally described by Bochner et al., J. Bacteriol. 1980 August; 143(2): 926-933, the subject matter of which is incorporated herein by reference. Glucose is a preferred fermentable carbon source for this microorganism.

A fermentable carbon source (e.g., carbohydrates and sugars), optionally a source of nitrogen and complex nutrients (e.g., corn steep liquor), additional media components such as vitamins, salts and other materials that can improve cellular growth and/or product formation, and water may be fed to the growth vessel for growth and sustenance of the microbial culture. Typically, the microbial culture is grown under aerobic conditions provided by sparging an oxygen-rich gas (e.g., air or the like). Typically, an acid (e.g., sulphuric acid or the like) and ammonium hydroxide are provided for pH control during the growth of the microbial culture.

In one example, the aerobic conditions in the growth vessel (provided by sparging an oxygen-rich gas) are switched to anaerobic conditions by changing the oxygen-rich gas to an oxygen-deficient gas (e.g., $CO_2$ or the like). The anaerobic environment triggers bioconversion of the fermentable carbon source to succinic acid in situ in the growth vessel. Ammonium hydroxide is provided for pH control during bioconversion of the fermentable carbon source to SA. The SA that is produced is at least partially if not totally neutralized to DAS due to the presence of the ammonium hydroxide, leading to the production of a broth comprising DAS. The $CO_2$ provides an additional source of carbon for the production of SA.

In another example, the contents of the growth vessel may be transferred via a stream to a separate bioconversion vessel for bioconversion of a carbohydrate source to SA. An oxygen-deficient gas (e.g., $CO_2$ or the like) is sparged in the bioconversion vessel to provide anaerobic conditions that trigger production of SA. Ammonium hydroxide is provided for pH control during bioconversion of the carbohydrate source to SA. Due to the presence of the ammonium hydroxide, the SA produced is at least partially neutralized to DAS, leading to production of a broth that comprises DAS. The $CO_2$ provides an additional source of carbon for production of SA.

In yet another example, the bioconversion may be conducted at relatively low pH (e.g., 3-6). A base (ammonium hydroxide or ammonia) may be provided for pH control during bioconversion of the carbohydrate source to SA. Depending of the desired pH, due to the presence or lack of the ammonium hydroxide, either SA is produced or the SA produced is at least partially neutralized to MAS, DAS, or a mixture comprising SA, MAS and/or DAS. Thus, the SA produced during bioconversion can be subsequently neutralized, optionally in an additional step, by providing either ammonia or ammonium hydroxide leading to a broth comprising DAS. As a consequence, a "DAS-containing fermentation broth" generally means that the fermentation broth comprises DAS and possibly any number of other components such as MAS and/or SA, whether added and/or produced by bioconversion or otherwise. Similarly, a "MAS-containing fermentation broth" generally means that the fermentation both comprises MAS and possibly any number of other components such as DAS and/or SA, whether added and/or produced by bioconversion or otherwise.

The broth resulting from the bioconversion of the fermentable carbon source (in either the vessel or the stream, depending on where the bioconversion takes place), typically contains insoluble solids such as cellular biomass and other suspended material, which are transferred via a stream to a clarification apparatus before distillation. Removal of insoluble solids clarifies the broth. This reduces or prevents fouling of subsequent distillation equipment. The insoluble solids can be removed by any one of several solid-liquid separation techniques, alone or in combination, including but not limited to, centrifugation and filtration (including, but not limited to ultra-filtration, micro-filtration or depth filtration).

The choice of filtration technique can be made using techniques known in the art. Soluble inorganic compounds can be removed by any number of known methods such as but not limited to ion-exchange, physical adsorption and the like.

An example of centrifugation is a continuous disc stack centrifuge. It may be useful to add a polishing filtration step following centrifugation such as dead-end or cross-flow filtration, which may include the use of a filter aide such as diatomaceous earth or the like, or more preferably ultra-filtration or micro-filtration. The ultra-filtration or micro-filtration membrane can be ceramic or polymeric, for example. One example of a polymeric membrane is SelRO MPS-U20P (pH stable ultra-filtration membrane) manufactured by Koch Membrane Systems (850 Main Street, Wilmington, Mass., USA). This is a commercially available polyethersulfone membrane with a 25,000 Dalton molecular weight cut-off which typically operates at pressures of 0.35 to 1.38 MPa (maximum pressure of 1.55 MPa) and at temperatures up to 50 C. Alternatively, a filtration step may be employed, such as ultra-filtration or micro-filtration alone.

The resulting clarified DAS-containing broth, substantially free of the microbial culture and other solids, is transferred via a stream to a distillation apparatus.

The clarified distillation broth should contain DAS and/or MAS in an amount that is at least a majority of, preferably at least about 70 wt %, more preferably 80 wt % and most preferably at least about 90 wt % of all the diammonium dicarboxylate salts in the broth. The concentration of DAS and/or MAS as a weight percent (wt %) of the total dicarboxylic acid salts in the fermentation broth can be easily determined by high pressure liquid chromatography (HPLC) or other known means.

Water and ammonia are removed from the distillation apparatus as an overhead, and at least a portion is optionally recycled via a stream to the bioconversion vessel (or the growth vessel operated in the anaerobic mode).

Distillation temperature and pressure are not critical as long as the distillation is carried out in a way that ensures that the distillation overhead contains water and ammonia, and the distillation bottoms comprises at least some MAS and at least about 20 wt % water. A more preferred amount of water is at least about 30 wt % and an even more preferred amount is at least about 40 wt %. The rate of ammonia removal from the distillation step increases with increasing temperature and also can be increased by injecting steam during distillation. The rate of ammonia removal during distillation may also be increased by conducting distillation under a vacuum or by sparging the distillation apparatus with a non-reactive gas such as air, nitrogen or the like.

Removal of water during the distillation step can be enhanced by the use of an organic azeotroping agent such as toluene, xylene, methylcyclohexane, methyl isobutyl ketone, cyclohexane, heptane or the like, provided that the bottoms contains at least about 20 wt % water. If the distillation is carried out in the presence of an organic agent capable of forming an azeotrope consisting of the water and the agent, distillation produces a biphasic bottoms that comprises an aqueous phase and an organic phase, in which case the aqueous phase can be separated from the organic phase, and the aqueous phase used as the distillation bottoms. Byproducts such as succinamide and succinimide are substantially avoided provided the water level in the bottoms is maintained at a level of at least about 30 wt %.

A preferred temperature for the distillation step is in the range of about 50 to about 300° C., depending on the pressure. A more preferred temperature range is about 15 to about 240° C., depending on the pressure. A distillation temperature of about 170 to about 270° C. is preferred. "Distillation temperature" refers to the temperature of the bottoms (for batch distillations this may be the temperature at the time when the last desired amount of overhead is taken).

Adding a water miscible organic solvent or an ammonia separating solvent facilitates deammoniation over a variety of distillation temperatures and pressures as discussed above. Such solvents include aprotic, bipolar, oxygen-containing solvents that may be able to form passive hydrogen bonds. Examples include, but are not limited to, diglyme, triglyme, tetraglyme, sulfoxides such as dimethylsulfoxide (DMSO), amides such as dimethylformamide (DMF) and dimethylacetamide, sulfones such as dimethylsulfone, gamma-butyrolactone (GBL), sulfolane, polyethyleneglycol (PEG), butoxytriglycol, N-methylpyrolidone (NMP), ethers such as dioxane, methyl ethyl ketone (MEK) and the like. Such solvents aid in the removal of ammonia from the DAS or MAS in the clarified broth. Regardless of the distillation technique, it is important that the distillation be carried out in a way that ensures that at least some MAS and at least about 20 wt % water remain in the bottoms and even more advantageously at least about 30 wt %. The distillation can be performed at atmospheric, sub-atmospheric or super-atmospheric pressures.

Under other conditions such as when the distillation is conducted in the absence of an azeotropic agent or ammonia separating solvent, the distillation is conducted at super atmospheric pressure at a temperature of greater than 100° C. to about 300° C. to form an overhead that comprises water and ammonia, and a liquid bottoms that comprises SA and at least about 20 wt % water. Super atmospheric pressure typically falls within a range of greater than ambient atmosphere up to and including about 25 atmospheres. Advantageously the amount of water is at least about 30 wt %.

The distillation can be a one-stage flash, a multistage distillation (i.e., a multistage column distillation) or the like. The one-stage flash can be conducted in any type of flasher (e.g., a wiped film evaporator, thin film evaporator, thermosiphon flasher, forced circulation flasher and the like). The multi-stages of the distillation column can be achieved by using trays, packing or the like. The packing can be random packing (e.g., Raschig rings, Pall rings, Berl saddles and the like) or structured packing (e.g., Koch-Sulzer packing, Intalox packing, Mellapak and the like). The trays can be of any design (e.g., sieve trays, valve trays, bubble-cap trays and the like). The distillation can be performed with any number of theoretical stages.

If the distillation apparatus is a column, the configuration is not particularly critical, and the column can be designed using well known criteria. The column can be operated in either stripping mode, rectifying mode or fractionation mode. Distillation can be conducted in either batch, semi-continuous or continuous mode. In the continuous mode, the broth may be fed continuously into the distillation apparatus, and the overhead and bottoms continuously removed from the apparatus as they are formed. The distillate from distillation is an ammonia/water solution, and the distillation bottoms is a liquid, aqueous solution of MAS and SA, which may also contain other fermentation by-product salts (i.e., ammonium acetate, ammonium formate, ammonium lactate and the like) and color bodies.

The distillation bottoms can be transferred via a stream to a cooling apparatus and cooled by conventional techniques. Cooling technique is not critical. A heat exchanger (with heat recovery) can be used. A flash vaporization cooler can be used to cool the bottoms down to about 15° C. Cooling to 0° C. typically employs a refrigerated coolant such as, for example, glycol solution or, less preferably, brine. A concentration step can be included prior to cooling to help increase product yield. Further, both concentration and cooling can be combined using methods well known in the art such as vacuum evaporation and heat removal using integrated cooling jackets and/or external heat exchangers.

Figure 3:
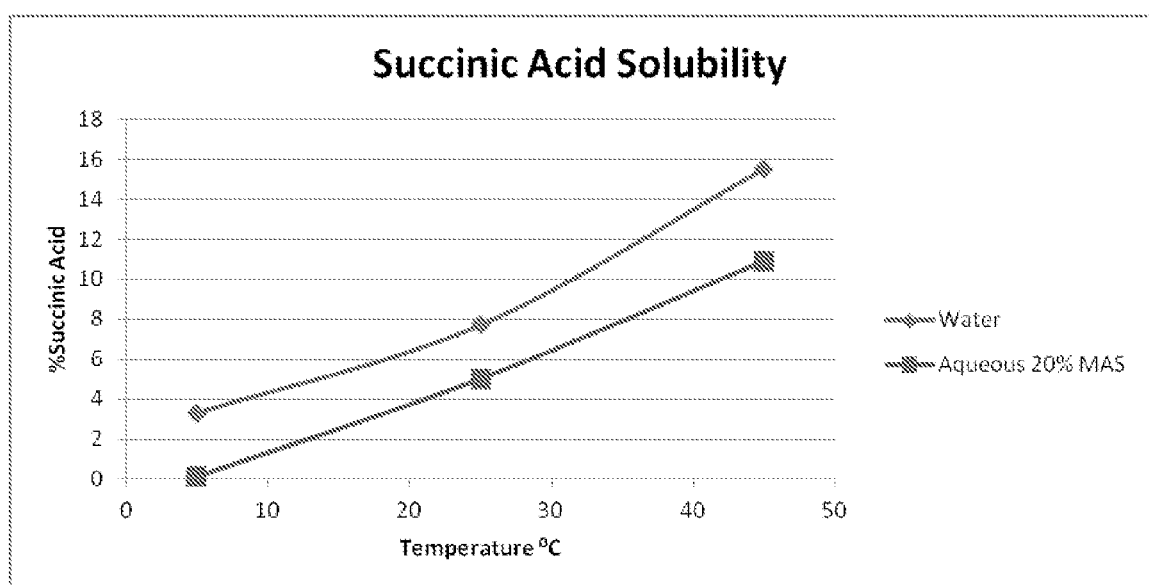
FIG. 3 is a graph showing the solubility of SA as a function of temperature in both water and a 20 wt % aqueous MAS solution.

We found that the presence of some MAS in the liquid bottoms facilitates cooling-induced separation of the bottoms into a liquid portion in contact with a solid portion that at least "consists essentially" of SA (meaning that the solid portion is at least substantially pure crystalline SA) by reducing the solubility of SA in the liquid, aqueous, MAS-containing bottoms. FIG. 3 illustrates the reduced solubility of SA in an aqueous 20 wt % MAS solution at various temperatures ranging from 5 to 45° C. We discovered, therefore, that SA can be more completely crystallized out of an aqueous solution if some MAS is also present in that solution. A preferred concentration of MAS in such a solution is about 20 wt % or higher. This phenomenon allows crystallization of SA (i.e., formation of the solid portion of the distillation bottoms) at temperatures higher than those that would be required in the absence of MAS.

The distillation bottoms may be fed via a stream to the separator for separation of the solid portion from the liquid portion. Separation can be accomplished via pressure filtration (e.g., using Nutsche or Rosenmond type pressure filters), centrifugation and the like. The resulting solid product can be recovered as a product and dried, if desired, by standard methods.

After separation, it may be desirable to treat the solid portion to ensure that no liquid portion remains on the surface(s) of the solid portion. One way to minimize the amount of liquid portion that remains on the surface of the solid portion is to wash the separated solid portion with water and dry the resulting washed solid portion. A convenient way to wash the solid portion is to use a so-called "basket centrifuge." Suitable basket centrifuges are available from The Western States Machine Company (Hamilton, Ohio, USA).

The liquid portion of the distillation bottoms (i.e., the mother liquor) may contain remaining dissolved SA, any unconverted MAS, any fermentation byproducts such as ammonium acetate, lactate, or formate, and other minor impurities. This liquid portion can be fed via a stream to a downstream apparatus. In one instance, the downstream apparatus may be a means for making a de-icer by treating in the mixture with an appropriate amount of potassium hydroxide, for example, to convert the ammonium salts to potassium salts. Ammonia generated in this reaction can be recovered for reuse in the bioconversion vessel (or the growth vessel operating in the anaerobic mode). The resulting mixture of potassium salts is valuable as a de-icer and anti-icer.

The mother liquor from the solids separation step can be recycled (or partially recycled) to a distillation apparatus via a stream to further enhance recovery of SA, as well as further convert MAS to SA.

HPLC can be used to detect the presence of nitrogen-containing impurities such as succinamide and succinimide. The purity of SA can be determined by elemental carbon and nitrogen analysis. An ammonia electrode can be used to determine a crude approximation of SA purity.

Depending on the circumstances and various operating inputs, there are instances when the fermentation broth may be a clarified MAS-containing fermentation broth or a clarified SA-containing fermentation broth. In those circumstances, it can be advantageous to add MAS, DAS and/or SA and, optionally, ammonia and/or ammonium hydroxide to those fermentation broths to facilitate the production of substantially pure SA. For example, the operating pH of the fermentation broth may be oriented such that the broth is a MAS-containing broth or a SA-containing broth. MAS, DAS, SA, ammonia and/or ammonium hydroxide may be optionally added to those broths to attain a broth pH preferably <6 to facilitate production of the above-mentioned substantially pure SA. In one particular form, it is especially advantageous to recycle SA, MAS and water from the liquid bottoms resulting from the distillation step into the fermentation broth and/or clarified fermentation broth. In referring to the MAS-containing broth, such broth generally means that the fermentation broth comprises MAS and possibly any number of other components such as DAS and/or SA, whether added and/or produced by bioconversion or otherwise.

The SA may be fed directly to a hydrogenation reactor. The preferred concentration of SA in the feed solution is about 4% to about 50% and more preferably about 4% to about 10%.

Figure 2:
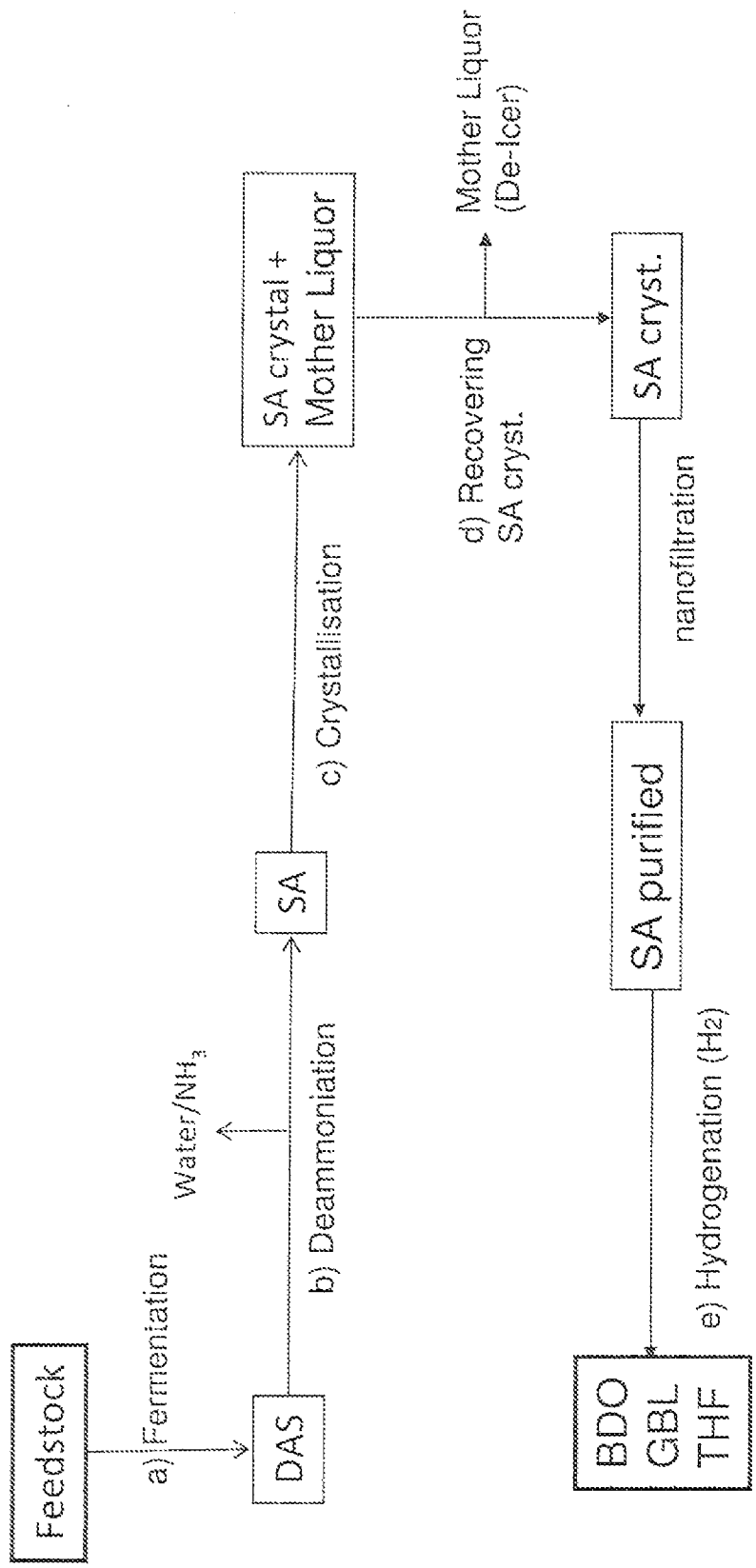
FIG. 2 schematically illustrates a fully integrated process for the hydrogenation of fermentation-derived SA to BDO, THF and GBL and depicts single-stage deammoniation of DAS to SA.

The SA solution can be further purified using nanofiltration as schematically shown in FIG. 2. Surprisingly, we observed that nanofiltration is useful in filtering out fermentation-derived impurities such as polypeptides and polysaccharides that impair the performance of structured hydrogenation catalysts.

Streams comprising SA as presented in FIGS. 1 and 2 may be contacted with hydrogen and a hydrogenation catalyst at elevated temperatures and pressures to produce a hydrogenation product comprising THF, BDO and GBL.

A principal component of the catalyst useful for hydrogenation of SA may be at least one from metal from palladium, ruthenium, rhenium, rhodium, iridium, platinum, nickel, cobalt, copper, iron and compounds thereof.

A chemical promoter may augment the activity of a catalyst. The promoter may be incorporated into the catalyst during any step in the chemical processing of the catalyst constituent. The chemical promoter generally enhances the physical or chemical function of the catalyst agent, but can also be added to retard undesirable side reactions. Suitable promoters include but are not limited to metals selected from tin, zinc, copper, gold, silver, and combinations thereof. The preferred metal promoter is tin. Other promoters that can be used are elements selected from Group I and Group II of the Periodic Table, for example.

The catalyst may be supported or unsupported. A supported catalyst is one in which the active catalyst agent is deposited on a support material by a number of methods, such as spraying, soaking or physical mixing, followed by drying, calcination, and if necessary, activation through methods such as reduction or oxidation. Materials frequently used as a support are porous solids with high total surface areas (external and internal) which can provide high concentrations of active sites per unit weight of catalyst. The catalyst support may enhance the function of the catalyst agent. A supported metal catalyst is a supported catalyst in which the catalyst agent is a metal.

A catalyst that is not supported on a catalyst support material is an unsupported catalyst. An unsupported catalyst may be platinum black or a Raney® (W.R. Grace & Co., Columbia, Md.) catalyst, for example. Raney® catalysts have a high surface area due to selectively leaching an alloy containing the active metal(s) and a leachable metal (usually aluminum). Raney® catalysts have high activity due to the higher specific area and allow the use of lower temperatures in hydrogenation reactions. The active metals of Raney® catalysts include at least one of nickel, copper, cobalt, iron, rhodium, ruthenium, rhenium, osmium, iridium, platinum, palladium and compounds thereof.

Promoter metals may also be added to the base Raney® metals to affect selectivity and/or activity of the Raney® catalyst. Promoter metals for Raney® catalysts may be selected from transition metals from Groups IIIA through VIIIA, IB and IIB of the Periodic Table of the Elements, for example. Examples of promoter metals include but are not limited to chromium, molybdenum, platinum, rhodium, ruthenium, osmium, and palladium, typically at about 2% by weight of the total metal, although other weight percentages are possible.

The catalyst support can be any solid, inert substance including, but not limited to, oxides such as silica, alumina and titania; barium sulfate; calcium carbonate; and carbons. The catalyst support can be in the form of powder, granules, pellets, or the like.

A preferred support material may be at least one of carbon, alumina, silica, silica-alumina, silica-titania, titania, titania-alumina, barium sulfate, calcium carbonate, strontium carbonate and compounds thereof. Supported metal catalysts can also have supporting materials made from one or more compounds. More preferred supports are carbon, titania and alumina, for example. Further preferred supports are carbons with a surface area greater than about 100 $m^2/g$. A further preferred support is carbon with a surface area greater than about 200 $m^2/g$. Preferably, the carbon has an ash content that is less than about 5% by weight of the catalyst support. The ash content is the inorganic residue (expressed as a percentage of the original weight of the carbon) which remains after incineration of the carbon.

A preferred content of the metal catalyst in the supported catalyst is from about 0.1% to about 20% of the supported catalyst based on metal catalyst weight plus the support weight. A more preferred metal catalyst content range is from about 1% to about 10% of the supported catalyst.

Combinations of metal catalyst and support system may include any one of the metals referred to herein with any of the supports referred to herein. Preferred combinations of metal catalyst and support include but are not limited to palladium on carbon, palladium on alumina, palladium on titania, platinum on carbon, platinum on alumina, platinum on silica, iridium on silica, iridium on carbon, iridium on alumina, rhodium on carbon, rhodium on silica, rhodium on alumina, nickel on carbon, nickel on alumina, nickel on silica, rhenium on carbon, rhenium on silica, rhenium on alumina, ruthenium on carbon, ruthenium on alumina and ruthenium on silica.

Further preferred combinations of metal catalyst and support include ruthenium on carbon, ruthenium on alumina, palladium on carbon, palladium on alumina, palladium on titania, platinum on carbon, platinum on alumina, rhodium on carbon, and rhodium on alumina.

A more preferred support is carbon. Further preferred supports are those, particularly carbon, that have a BET surface area greater than about 2,000 $m^2/g$. Further preferred supports are those, particularly carbon, that have a surface area of about 300 $m^2/g$ to about 1,000 $m^2/g$.

Typically, such hydrogenation reactions are performed at temperatures from about 100° C. to about 300° C. in reactors maintained at pressures from about 1000 to about 3000 psig (7×10~ to about 21×10~Pa gage).

The method of using the catalyst to hydrogenate a SA containing feed can be performed by various known modes of operation. Thus, the overall hydrogenation process can be performed with a fixed bed reactor, various types of agitated slurry reactors, either gas or mechanically agitated, or the like. The hydrogenation process can be operated in either a batch or continuous mode, wherein an aqueous liquid phase containing the precursor to hydrogenate contacts a gaseous phase containing hydrogen at elevated pressure and the particulate solid catalyst.

When the catalyst is used to produce BDO and THF at a desired or controlled molar ratio, hydrogenation is preferably performed at a temperature above about 150° C. and below about 260° C. To obtain a high BDO to THF ratio, the hydrogenation to those desired products should advantageously be performed at or near the lower end of this temperature range. The method and conditions will also advantageously influence the molar ratio during hydrogenation. For example, the liquid phase removal of products from the hydrogenation reactor tends to enhance and maximize BDO production rather than THF. In contrast, continuous vapor removal of product from the hydrogenation reactor tends to maximize THF production at the expense of BDO. Thus, as a practical consideration, low temperature liquid product removal intended to favor BDO production favors the use of fixed bed catalytic reactors. On the other hand, vapor phase product removal intended to favor tetrahydrofuran production favors the use of slurry or stirred reactors.

Temperature, solvent, catalyst, reactor configuration, pressure and mixing rate are parameters that may affect aspects of the hydrogenation. The relationships among these parameters may be adjusted to effect the desired conversion, reaction rate, and selectivity in the reaction of the process.

A preferred temperature is from about 25° C. to 350° C., more preferably from about 100° C. to about 350° C., and most preferred from about 150° C. to 300° C. The hydrogen pressure is preferably about 0.1 to about 30 MPa, more preferably about 1 to 25 MPa, and most preferably about 1 to 20 MPa.

The reaction may be performed neat, in water or in the presence of an organic solvent. Water is a preferred solvent. Useful organic solvents include but are not limited to hydrocarbons, ethers, and alcohols, for example. Alcohols are most preferred, particularly lower alkanols such as methanol, ethanol, propanol, butanol, and pentanol. Selectivity is in the range of at least about 70%. Selectivity of at least about 85% is typical. Selectivity is the weight percent of the converted material that is THF, BDO and GBL, where the converted material is the portion of the starting material that participates in the hydrogenation reaction.

The processes may be carried out in batch, sequential batch (i.e., a series of batch reactors) or in continuous mode in equipment customarily employed for continuous processes (see, for example, H. S. Fogler, *Elementary Chemical Reaction Engineering*, Prentice-Hall, Inc., NJ, USA). The condensate water formed as the product of the reaction is removed by separation methods customarily employed for such separations.

A preferred hydrogenation reactor is operated under hydrogen pressure and in the presence of structured catalyst chosen from at least one among Ru, Re, Sn, Pb, Ag, Ni, Co, Zn, Cu, Cr or Mn in catalytic amounts. The hydrogen pressure and the temperature of the reactor are controlled to obtain the desired hydrogenation product. Typically, the reactor feed for hydrogenation is maintained from 100° C. to 210° C., but most preferably about 135° C. to 150° C.

BDO, THF, and GBL can be separated by known distillation methods. Further, GBL can be partially or fully recycled to the hydrogenation step to maximize the yield of BDO, THF, or both.

EXAMPLES

The processes are illustrated by the following non-limiting representative examples. In the first two examples, a synthetic, aqueous DAS solution was used in place of an actual clarified DAS-containing fermentation broth. The other examples employed an actual clarified DAS-containing fermentation broth.

For the first two examples, the use of a synthetic DAS solution is believed to be a good model for the behavior of an actual broth in our processes because of the solubility of the typical fermentation by-products found in actual broth. The major by-products produced during fermentation are ammonium acetate, ammonium lactate and ammonium formate. Ammonium acetate, ammonium lactate and ammonium formate are significantly more soluble in water than SA, and each is typically present in the broth at less than 10% of the DAS concentration. In addition, even when the acids (acetic, formic and lactic acids) were formed during the distillation step, they are miscible with water and will not crystallize from water. This means that the SA reaches saturation and crystallizes from solution (i.e., forming the solid portion), leaving the acid impurities dissolved in the mother liquor (i.e., the liquid portion).

Example 1

This experiment shows the conversion of DAS to SA in an aqueous media.

An experiment was conducted in a 300 ml Hastelloy C stirred Parr reactor using a 15% (1.0 M) synthetic DAS solution. The reactor was charged with 200 g of solution and pressurized to 200 psig. The contents were then heated to begin distillation, bringing the temperature to approximately 200° C. Ammonia and water vapor were condensed overhead with cooling water and collected in a reservoir. Fresh water was pumped back to the system at a rate equal to the make rate (approximately 2 g/min) to maintain a constant succinate concentration and volume of material. The run continued for 7 hours. At the end of the run, analysis of the mother liquor showed 59% conversion to SA, 2.4% to succinamic acid, and 2.9% to succinimide. Cooling the mother liquor would result in a liquid portion and a solid portion that would be substantially pure SA.

Example 2

This example demonstrates the effect of solvents on ammonia evolution from aqueous DAS. Run 10 is the control experiment where no solvent is present.

The outer necks of a three neck 1-L round bottom flask were fitted with a thermometer and a stopper. The center neck was fitted with a five tray 1" Oldershaw section. The Oldershaw section was topped with a distillation head. An ice cooled 500 mL round bottom flask was used as the receiver for the distillation head. The 1-L round bottom flask was charged with distilled water, the solvent being tested, SA and concentrated ammonium hydroxide solution. The contents were stirred with a magnetic stirrer to dissolve all the solids. After the solids dissolved, the contents were heated with the heating mantle to distill 350 g of distillate. The distillate was collected in the ice cooled 500 mL round bottom flask. The pot temperature was recorded as the last drop of distillate was collected. The pot contents were allowed to cool to room temperature and the weight of the residue and weight of the distillate were recorded. The ammonia content of the distillate was then determined via titration. The results were recorded in Tables 1 and 2.

TABLE 1

| | Run # | | | | |
|---|---|---|---|---|---|
| | 1 | 2 | 3 | 4 | 5 |
| Name of Acid charged | Succinic | Succinic | Succinic | Succinic | Succinic |
| Wt Acid Charged (g) | 11.8 | 11.81 | 11.83 | 11.8 | 11.78 |
| Moles Acid Charged | 0.1 | 0.1 | 0.1 | 0.1 | 0.1 |
| Wt 28% NH3 Solution Charged (g) | 12.76 | 12.78 | 12.01 | 12.98 | 13.1 |
| Moles NH3 Charged | 0.21 | 0.21 | 0.2 | 0.215 | 0.217 |
| Name of Solvent | DMSO | DMF | NMP | sulfolane | triglyme |
| Wt Solvent Charged (g) | 400.9 | 400 | 400 | 400 | 400 |
| Wt Water Charged (g) | 400 | 400 | 400 | 400 | 401 |
| Wt Distillate (g) | 350.1 | 365.9 | 351.3 | 352.1 | 351.2 |
| Wt Residue (g) | 467.8 | 455 | 460.5 | 457.1 | 473 |
| % Mass Accountability | 99.1 | 99.6 | 98.5 | 98.1 | 99.8 |
| Wt % NH3 in distillate (titration) | 0.91 | 0.81 | 0.78 | 0.71 | 0.91 |
| Moles NH3 in distillate | 0.187 | 0.174 | 0.161 | 0.147 | 0.188 |
| % NH3 removed in Distillate | 89 | 83 | 81 | 66 | 86 |
| % First NH3 removed in Distillate | 100 | 100 | 100 | 100 | 100 |
| % Second NH3 removed in Distillate | 78 | 66 | 62 | 32 | 72 |
| Final Pot Temp (° C.) | 138 | 114 | 126 | 113 | 103 |
| Final DAS/MAS/SA ratio | 0/22/78 | 0/34/66 | 0/38/62 | 0/68/32 | 0/28/72 |

TABLE 2

| | Run # | | | | |
|---|---|---|---|---|---|
| | 6 | 7 | 8 | 9 | 10 |
| Name of Acid charged | Succinic | Succinic | Succinic | Succinic | Succinic |
| Wt Acid Charged (g) | 11.84 | 11.81 | 11.8 | 11.81 | 11.8 |
| Moles Acid Charged | 0.1 | 0.1 | 0.1 | 0.1 | 0.1 |
| Wt 28% NH3 Solution Charged (g) | 12.11 | 12.11 | 12.1 | 12.15 | 12.1 |
| Moles NH3 Charged | 0.2 | 0.2 | 0.2 | 0.2 | 0.2 |
| Name of Solvent | Dowanol TPM | Tetraglyme | Tetra PentaEG | HeavyMe GlyEther | none |
| Wt Solvent Charged (g) | 400.1 | 400 | 400 | 400.1 | 0 |
| Wt Water Charged (g) | 400 | 400 | 400 | 400.1 | 800 |
| Wt Distillate (g) | 350 | 345 | 350 | 349 | 351 |
| Wt Residue (g) | 468.4 | 473.8 | 465 | 470.4 | 466 |
| % Mass Accountability | 99.3 | 99.4 | 98.9 | 99.4 | 99.2 |
| Wt % NH3 in distillate (titration) | 0.58 | 0.62 | 0.55 | 0.6 | 0.13 |

TABLE 2-continued

| | Run # | | | | |
|---|---|---|---|---|---|
| | 6 | 7 | 8 | 9 | 10 |
| Moles NH3 in distillate | 0.119 | 0.126 | 0.113 | 0.123 | 0.027 |
| % NH3 removed in Distillate | 60 | 63 | 57 | 62 | 13.4 |
| % First NH3 removed in Distillate | 100 | 100 | 100 | 100 | 27 |
| % Second NH3 removed in Distillate | 20 | 26 | 14 | 24 | 0 |
| Final Pot Temp (° C.) | 104 | 110 | 115 | 113 | 100 |
| Final DAS/MAS/SA ratio | 0/80/20 | 0/74/26 | 0/86/14 | 0/76/24 | 83/27/0 |

Example 3

This example used a DAS-containing, clarified fermentation broth derived from a fermentation broth containing *E. coli* strain ATCC PTA-5132.

The initial fermentation broth was clarified, thereby resulting in a clarified fermentation broth containing ~4.5% diammonium succinate (DAS). That clarified broth was used to produce crystalline SA as follows. The broth was first concentrated to approximately 9% using an RO membrane and then subjected to distillation at atmospheric pressure to further concentrate the broth to around 40%.

The concentrated broth was used as the starting material for conversion of DAS to SA, carried out batchwise in a 300 ml Parr reactor. A 200 g portion of the solution was reacted at 200° C./200 psig for 11 hours. As the reaction proceeded, water vapor and ammonia liberated from the DAS were condensed and collected overhead. Condensate was collected at about 2 g/min, and makeup water was fed back to the system at approximately the same rate.

Multiple samples were taken throughout the experiment. Samples taken early in the reaction indicated the presence of succinamide, succinamic acid, and succinimide. However, these nitrogen-containing byproducts decreased throughout the experiment. Conversion to SA was observed to be 55% in the final bottoms sample. The final solution was concentrated by evaporation and cooled to 4° C. The resulting crystalline solids were isolated via vacuum filtration, washed with ice water and dried under vacuum. The product (7 g) was essentially pure SA as determined by HPLC.

Example 4

A 500 mL round bottom flask was charged with 80 g of an aqueous 36% DAS solution and 80 g of triglyme. The flask was fitted with a 5 tray 1" glass Oldershaw column section which was topped with a distillation head. An addition funnel containing 3300 g of water was also connected to the flask. The flask was stirred with a magnetic stirrer and heated with a heating mantel. The distillate was collected in an ice cooled receiver. When the distillate started coming over the water in the addition funnel was added to the flask at the same rate as the distillate was being taken. A total of 3313 g of distillate was taken. The distillate contained 4.4 g of ammonia, as determined by titration. This means ~37% of the DAS was converted to SA with the rest being converted to MAS. The residue in the flask was then placed in an Erlenmeyer flask and cooled to −4° C. while stirring. After stirring for 30 minutes the slurry was filtered while cold yielding 7.1 g of solids. The solids were dissolved in 7.1 g of hot water and then cooled in an ice bath while stirring. The cold slurry was filtered and the solids dried in a vacuum oven at 100° C. for 2 hrs yielding 3.9 g of SA. HPLC analysis indicated that the solids were SA with 0.099% succinamic acid present.

Example 5

A pressure distillation column was made using an 8 ft long 1.5" 316 SS Schedule 40 pipe that was packed with 316 SS Propak packing. The base of the column was equipped with an immersion heater to serve as a reboiler. Nitrogen was injected into the reboiler via a needle valve to pressure. The overhead of the column had a total take-off line which went to a 316 SS shell and tube condenser with a receiver. The receiver was equipped with a pressure gauge and a back pressure regulator. Material was removed from the overhead receiver via blowcasing through a needle valve. Preheated feed was injected into the column at the top of the packing via a pump along with a dilute 0.4% sodium hydroxide solution. Preheated water was also injected into the reboiler via a pump. This column was first operated at 50 psig pressure which gave a column temperature of 150° C. The top of the column was fed a 4.7% DAS containing broth at a rate of 8 mL/min along with 0.15 mL/min of 0.4% sodium hydroxide solution. Water was fed to the reboiler at a rate of 4 mL/min. The overhead distillate rate was taken at 8 mL/min and the residue rate was taken at 4 mL/min. A total of 2565 g of broth was fed to the column along with 53 g of 0.4% sodium hydroxide solution. A total of 2750 g of distillate was taken and 1269 g of residue taken during the run. Titration of the distillate indicated that ~71% of the total ammonia contained in the DAS was removed (i.e. the residue was a 42/58 mixture of SA/MAS). The composited residue was then fed back to the same column the next day under the following conditions; pressure 100 psig and temperature 173° C. The composited residue was fed to the top of the column at 4 mL/min along with 0.15 mL/min of 0.4% sodium hydroxide solution. The reboiler was fed water at 9.2 mL/min. A total of 1240 g of residue from the previous day was fed to the column along with 58 g of sodium hydroxide solution and 2890 g of water. A total of 3183 g of distillate was taken along with 1132 g of residue during the run. Titration of the distillate revealed an additional ~14% of the ammonia was removed yielding a 70/30 mixture of SA/MAS in the residue.

Examples 6-13

A series of batch hydrogenation reactions are performed to evaluate the effectiveness of the catalysts in the hydrogenation of fermentation-derived SA. The reactions are conducted in a stirrable 125 ml autoclave rated up to 2,500 psig.

Hydrogenation experiments are conducted by reducing the catalysts in situ for determination of catalyst compositions suitable for hydrogenation of fermentation-derived SA. The experiments are conducted in the 125 ml autoclave as follows: (1) 0.5100 grams of a 1% ruthenium solution derived from $RuCl_3 \cdot xH_2O$, 0.2780 g of a $HReO_4$ solution (7.7% Re from $Re_2O_7$), 0.5035 g of particulate acidic carbon (BET 1,500 $m_2/g$), an appropriate amount of 12.5% Sn solution prepared from 5 $nCl_4;5H2O$, and 35 g of 7% aqueous SA solution are mixed in the autoclave; (2) Hydrogen is charged to the reactor to 1,200 psig; (3) The reactor contents are heated to 250° C. at 700 rpm and maintained at 250° C. for 3 hours; (4) The reactor is cooled and vented; and (5) A sample of the slurry in the reactor is filtered and analyzed for BDO, THF, GBL, 1-propanol, and n-butanol using gas chromatography.

Hydrogenation experiments are also conducted by pre-reducing the catalysts deposited on a support to determine catalysts compositions and supports suitable for hydrogenation of fermentation-derived SA. The catalyst is prepared as follows: (1) 2.0305 grams of 1% ruthenium solution derived from $RuCl_3 \cdot xH_2O$, 1.104 grams of 7.7% rhenium solution derived from $HReO_4$, appropriate amount of 12.5% Sn solution prepared from $SnCl_4;5H2O$, and 2.03 grams of particulate carbon support (average particle size about 20 micron) characterizes as intrinsically acidic (pH=4-4.5) with BET surface area of about 1,500 $m^2/g$ are slurried; (2) The slurry is dried at about 100-120° C., under vacuum and nitrogen purge; (3) The catalysts is reduced under hydrogen-helium flow for about 8 hours at about 300° C.; (4) The catalysts is cooled under helium to about 50° C. and passivated for 30 minutes under 1% $O_2$ in $N_2$. The hydrogenation experiments are conducted in the 125 ml autoclave as follows: (1) About 0.1 to 0.5 g of the catalyst and 35 g of 7% aqueous SA solution are mixed in the autoclave; (2) Hydrogen is charged to the reactor to 1,200 psig; (3) The reactor contents are heated to 250° C. at 700 rpm and maintained at 250° C. for 3 hours; (4) The reactor is cooled and vented; and (5) A sample of the slurry in the reactor is filtered and analyzed for BDO, THF, GBL, 1-propanol, and n-butanol using gas chromatography.

Hydrogenation of SA crystallized from simulated broth composed of reagent grade chemicals and de-ionized water is conducted to determine the effectiveness of the catalysts for SA hydrogenation. SA for hydrogenation is prepared as follows: (1) an aqueous solution consisting of 25% (wt.) SA, 2.5% (wt.) acetic acid, 0.25% (wt.) formic acid, and 0.25% (wt.) lactic acid is prepared at 80° C. in a jacketed kettle equipped with a reflux condenser; (2) The hot solution is cooled to 20° C. by cooling the solution over a 3 hour period following a linear cooling profile; (3) The solution is seeded with 0.1 g of SA crystals at 75° C.; (4) The slurry is allowed to equilibrate at 20° C. for 1 hour; (5) The slurry is filtered with vacuum filtration and washed with 20 g of water; (6) 50 g of the cake (10% wt. moisture) is dissolved in 593 g of deionized water (7% wt. solution).

Hydrogenation of SA crystallized from fermentation-derived broth is conducted to establish the effect of carryover impurities from fermentation. Fermentation-derived SA for hydrogenation is prepared as follows: (1) A fermentation-derived broth containing 4.5% (wt.) DAS, 0.45% (wt.) ammonium acetate, 0.05% (wt.) ammonium formate, and 0.05% (wt.) ammonium lactate is deammoniated and concentrated resulting in a greater than 25% SA solution; (2) The hot solution is cooled to 20° C. by cooling the solution over a 3 hour period following a linear cooling profile; (3) The solution is seeded with 0.1 g of SA crystals at 75° C.; (4) The slurry is allowed to equilibrate at 20° C. for 1 hour; (5) The slurry is filtered with vacuum filtration and washed with 20 g of water; (6) 50 g of the cake (10% wt. moisture) is dissolved in 593 g of deionized water (7% wt. solution).

Representative results are presented in Examples 6-13 in Table 3.

TABLE 3

Representative hydrogenation results

| Ex. | Catalysts | SA | BDO | THF | GBL | PrOH | BuOH |
|---|---|---|---|---|---|---|---|
| 6 | 1% Ru:4% Re [a] | S | 0.08 | 16.9 | 0.08 | 1.45 | 1.21 |
| 7 | 1% Ru:4% Re [a] | F | 0.08 | 16.9 | 0.08 | 1.45 | 1.21 |
| 8 | 1% Ru:0.8% Re:0.4% [a] | S | | | | | |
| 9 | 1% Ru:0.8% Re:0.4% [a] | F | | | | | |
| 10 | 1% Ru:4% Re [b] | S | 0.88 | 14.8 | 0.29 | 2.16 | 1.59 |
| 11 | 1% Ru:4% Re [b] | F | 0.88 | 14.8 | 0.29 | 2.16 | 1.59 |
| 12 | 1% Ru:0.8% Re:0.4% [b] | S | | | | | |
| 13 | 1% Ru:0.8% Re:0.4% [b] | F | | | | | |

S = succinic acid derived from simulated broth derived from reagent chemicals,
F = succinic acid derived from fermentation broth,
[a] = catalyst reduced in situ,
[b] = Pre-reduced catalytst,
PrOH = propanol, and
BuOH = butanol.

Although our processes have been described in connection with specific steps and forms thereof, it will be appreciated that a wide variety of equivalents may be substituted for the specified elements and steps described herein without departing from the spirit and scope of this disclosure as described in the appended claims.

The invention claimed is:

1. A process for making a hydrogenated product comprising:
    (a) Providing a clarified MAS-containing fermentation broth;
    (b) distilling the broth under super atmospheric pressure at a temperature of >100° C. to about 300° C. to form an overhead that comprises water and ammonia, and a liquid bottoms that comprises SA, and at least about 20 wt % water;
    (c) cooling and/or evaporating the bottoms to attain a temperature and composition sufficient to cause the bottoms to separate into a liquid portion and a solid portion that is substantially pure SA;
    (d) separating the solid portion from the liquid portion;
    (e) recovering the solid portion;
    (f) hydrogenating the solid portion in the presence of at least one hydrogenation catalyst to product the hydrogenated product comprising at least one of THF, GBL and BDO; and
    (g) recovering the hydrogenated product.

* * * * *